(12) United States Patent
Shioya

(10) Patent No.: US 6,506,406 B1
(45) Date of Patent: Jan. 14, 2003

(54) SOFT CAPSULE CONTAINING MASTIC OIL THEREIN

(75) Inventor: Masaaki Shioya, Numazu (JP)

(73) Assignees: Sansho Pharmaceutical Co., Ltd., Shimizu (JP); Nihonyakugyo Co., Ltd., Numazu (JP); California Functional Foods, Inc., Ashland, OR (US)

( * ) Notice: Subject to any disclaimer, the term of this patent is extended or adjusted under 35 U.S.C. 154(b) by 0 days.

(21) Appl. No.: 09/706,777

(22) Filed: Nov. 7, 2000

(30) Foreign Application Priority Data

Nov. 8, 1999 (JP) ............................. 11-316202

(51) Int. Cl.$^7$ ............................. A61K 9/48; A61K 9/66; A61K 9/14; A61K 9/50; A61K 35/78
(52) U.S. Cl. ........................ 424/451; 424/455; 424/463; 424/489; 424/500; 424/725; 424/776; 514/925
(58) Field of Search .................... 424/451, 455, 424/463, 489, 500, 725, 976; 514/925

(56) References Cited

U.S. PATENT DOCUMENTS

| | | | | |
|---|---|---|---|---|
| 4,428,927 A | * | 1/1984 | Ebert et al. | 424/37 |
| 4,999,341 A | * | 3/1991 | Ferro | 514/33 |
| 5,063,210 A | * | 11/1991 | Lange, III et al. | 514/54 |
| 5,364,636 A | * | 11/1994 | Ochi | 424/456 |
| 5,616,570 A | * | 4/1997 | Lange, III et al. | 514/54 |

OTHER PUBLICATIONS

Medicinal Plants of China (vol. 1), p. 72; James A. Duke and Edward S. Ayensu; Copyright 1985 by Reference Publications, Inc.*

* cited by examiner

Primary Examiner—Thurman K. Page
Assistant Examiner—Humera N. Sheikh
(74) Attorney, Agent, or Firm—Oliff & Berridge, PLC

(57) ABSTRACT

A soft capsule containing oil produced by dissolving mastic in oils and fats. The capsule may further contain amphipathic substance, chitin or chitosan. The capsule serves to remove and inhibit helicobacter pyloric bacteria, as well as to remove smell of feces. The soft capsule containing mastic conceals strong and unacceptable taste of mastic, is easy to be ingested, and has long and direct effect to the stomach.

12 Claims, No Drawings

SOFT CAPSULE CONTAINING MASTIC OIL THEREIN

BACKGROUND OF THE INVENTION

1. Field of the Invention

The present invention relates to a soft capsule containing mastic oil therein, and more particularly, the present invention relates to a soft capsule in which oil produced by dissolving mastic into oils and fats is contained.

2. Description of the Related Art

Mastic is a kind of resin in transparent and colorless, or somewhat in light-yellow color. Mastic is originally in a form of pine-tree gum produced from an anacardiaceous plant which is native in Khios Island, Greece, and is used as the material for chewing gums, that is, as the natural base for producing the gum. Recently, it has been reported several times that mastic has effects of removal and inhibitory action against helicobacter pyloric bacteria. Consequently, mastic attracts a great deal of attention as one of the material for health food.

The helicobacter pyloric bacterium is a Gram-negative bacterium which has been supposed to cause several kinds of digestive organ disease such as the chronic gastris, gastric ulcer, duodenal ulcer, stomach cancer, etc., and it has been said that the helicobacter pyloric bacteria live in the stomach of more than 80% of Japanese people who are 50 years old or more. Thus the removal and inhibition of multiplication of the helicobacter pyloric bacteria are believed to be one of the most practical and effective measures to prevent the occurrence of digestive organ disease.

However, since the helicobacter pyloric bacteria live deep in the epithelia of the mucous membrane cells which are positioned at the lowest part of the mucous strain (the mucous strain protects the inner wall of the stomach against the gastric juices), and since the helicobacter pyloric bacteria themselves have the defense effect against the stomach acids, the removal and inhibition thereof are quite difficult even by any pharmaceutical such as an antibiotic or an antibacterial agent. In addition, since there may often be the case that the medication of pharmaceuticals for a long period or the increase of amount of pharmaceuticals should be required;, there arises an anxiety of the side effect by these pharmaceuticals.

Therefore, since there has been awaited to be provided with the medicine which has no side effect and at. the same time has the considerable effects for removal and inhibition of the helicobacter pyloric bacteria, and since mastic may serve as a food material, the discovery of the removal and inhibitory effects of mastic as to the helicobacter pyloric bacteria is the good news for those who suffer from the digestive organ disease.

However, as mastic has the anti-soluble characteristic and the strong and unacceptable taste, the production of health food by using mastic would require several limitations. Thus, although there have been several kinds of health food using mastic, such as that in a form of chewing gum with the exceedingly sweet taste, or that containing mastic in a hard capsule after coarsely crushing mastic to be the granulated powder, they would be the limit of variation of health food containing mastic.

With regard to the health food according to the prior art as above discussed, in which mastic is used, it is insufficient to remove and inhibit the helicobacter pyloric bacteria, as will be discussed later in the experimental data of the present invention. The main reason is that, according to the prior art, since mastic has been used in an original solid form, even if the solid mastic is ingested, mastic will not sufficiently infiltrate into the epithelia of the mucous membrane cells. Consequently, the effect of mastic against the helicobacter pyloric bacteria will tend to be indirect and for the short time.

SUMMARY OF THE INVENTION

In the light of problems which have been described as above, the object of the present invention is to provide a composition containing mastic, with no side effect to human being, and with considerable effect to remove and inhibit the helicobacter pyloric bacteria.

For the object as above discussed, the inventor devoted himself to the research of composition by using mastic which has the good effect to remove and inhibit the helicobacter pyloric bacteria, and completed the present invention. According to the present invention, mastic is first dissolved in oils and fats such as a vegetable oil, animal oil, mineral oil, etc., in order to obtain mastic oil. Then, the mastic oil is filled in a soft capsule, or the mastic oil to which an amphipathic substance is added is filled in the soft capsule, or the mastic oil to which chitin or chitosan is added is filled in the soft capsule. The thus produced soft capsule has been proven to have the considerable effect to remove and inhibit the helicobacter pyloric bacteria.

According to claim 1 of the present invention, there is provided a soft capsule containing as contents oil which is produced by dissolving mastic in oils and fats.

According to claims 2 and 3, the soft capsule further comprises amphipathic substance added to the oils and fats. The amphipathic substance may be surfactant, ethanol or ethanol solution.

According to claims 4, 5 and 6, the soft capsule further comprises chitin or chitosan added to the oils and fats.

According to claims 7 through 12, the soft capsule serves the reduction effect of smell of feces.

DETAILED DESCRIPTION OF THE INVENTION

An embodiment of the present invention will now be, described in detail.

Oils and fats used in the present invention would mean oily substances contained in vegetable, animal, mineral, etc., and would also mean their products, such as the oils and fats themselves, or compound lipid such as phospholipid, or was, fatty acid, tryglyceride, etc.

The oily substances contained in vegetables, and their products, would mean vegetable oils and their products, such as the oils and fats, wax, phospholipid, etc., contained in the leaf, the seed or the fruit of vegetable. These would cover, for example, safflower oil, corn oil, olive oil, rape seed oil, rice oil, soybean oil, soybean lecithin, carnauba wax, candelilla wax, linoleic acid, linolenic acid, oleic acid, middle-chain fatty acid, coconut hardened oil, rape seed hardened oil, tocopherol, Beta-carotene, retinol, etc.

The oily substances contained in animals, and their products, would mean animal oils and their products, such as the oils and fats, was, phospholipid, etc., contained in the subcutaneous tissue, the abdominal cavity, the liver, the secretion of animal. These would cover, for example, fish oil such as sardine oil, tuna oil, cod-liver oil, squalene, and whale oil, beef lard, pork lard, egg yolk lecithin, arachidonic acid, bees wax, lanolin, beef hardened oil, pork hardened oil, etc. The mineral oil would cover paraffin, fluid paraffin, etc.

The oils and fats of which polarity are higher may have better solubility of mastic, thus may be a good solvent. Therefore, as compared with the oils and fats containing much amount of long-chain fatty acid, those containing much amount of middle- or short-chain fatty acid may have better solubility of mastic. As compared with the oils and fats containing much amount of triglyceride, those having much amount of monoglyceride or diglyceride may have better solubility of mastic.

The anphipathic substance would mean the substance which is soluble both in water soluble ingredient and in oil soluble ingredient. This would cover, for example, surfactant, lower alcohol such as ethanol, and its aqueous solution.

The surfactant would mean those having the effects of emulsification, solubilization or dispersion between the water soluble substance and the oil soluble substance. This would cover, for example, soybean lecithin, egg yolk lecithin, soybean saponin, bile acid, glycerin fatty acid ester, polyglycerin fatty acid ester, sorbitan fatty acid ester, cane sugar fatty acid ester, propylene glycol fatty acid ester.

Chitin, which is contained in large quantities in crustaceous animals such as crab, shrimp, krill, etc., would mean a natural polymer substance, as well as the hydrolysate thereof, consisting the bond of N-acetyl glucosamine in a form of normal chain.

Chitosan would mean a polymer substance, as well as the hydrolysate thereof, which is obtained by deacetylation. of chitin.

The oils and fats, the amphipathic substance, chitin and chitosan used in the present invention, are of course not limited to the examples discussed above. The oils and fats, amphipathic substance, chitin and chitosan may be used independently or by any combination thereof.

The concentration of mastic in the soft capsule, that is the concentration of the oil produced by dissolving mastic in the oils and fats, is not especially limited. However, the higher the concentration becomes, the higher the viscosity of the contents of the soft capsule would become, which might result in the inappropriate and exceeding viscosity of the. contents for producing the soft capsule. Further, under such an exceeding concentration, there may be a case that the mastic which has once been dissolved would crystallized again at a lower temperature. Thus, it may be concluded that the preferable concentration of mastic in the contents of the soft capsule is not more than 90 wt %, and the preferable concentration of the oils and fats in the contents of the soft capsule is not less than 10 wt %.

The concentration of the amphipathic substance is also not especially limited. However, when the amphipathic substance should be added, considering the effect of the amphipathic substance as an additive, the preferable concentration in the contents of the soft capsule is between 0.1 wt % and 50 wt %.

The concentration of chitin or chitosan is also not especially limited, However, when chitin or chitosan should be added, considering the appropriate concentration thereof for producing the soft capsule likewise the case of mastic, the preferable concentration in the contents of the soft capsule is between 0.1 wt % and 50 wt % in total.

With regard to the exploitation of the present invention, the method and apparatus for producing ordinary soft capsules in the prior art may be utilized without any modification, and no advanced manufacturing technology is required.

Further, when necessary, the soft capsule according to the present invention in which the oil produced by dissolving mastic in the oils and fats is contained, may further contain any additive or ingredient, such as food material, health food material, medicine, or any other substance for removal and inhibition of the helicobacter pyloric bacteria.

It is of course possible to further add any colorant, sweetener or spice, which may ordinarily be added to pharmaceuticals, medicines or foods, to the contents of the soft capsule.

The soft capsule containing the oil produced by dissolving mastic in the oils and fate according to the present invention has the merits as follows.

① Since the contents of the soft capsule include the mastic fluid which is produced by dissolving mastic in the oils and fats, as compared with the health foods in the prior art which containing solid mastic, the soft capsule according to the present invention, after being ingested, may be dispersed everywhere inside the stomach more easily. Consequently, mastic may directly and easily become in contact with the helicobacter pyloric bacteria, thus the good effect for removal and inhibition of the helicobacter pyloric bacteria may be obtained.

Further, despite that mastic is dissolved in the oils and fats to be in a form of liquid, since the thus obtained. mastic fluid is contained in the soft capsule, the product according to the present invention can be treated almost as the solid product, such as a health food in a form of chewing gum, or a health food contained in a hard capsule. Thus the product according to the present invention may provide users with the convenient handling thereof, and in addition, since the outer surface of the soft capsule conceals the strong and unacceptable taste of mastic, uses may ingest the product easily.

② In regard to the contents of the soft capsule which has been produced by dissolving mastic in the oils and fats, the case when the amphipathic substance is further added, will now be discussed. In this case, in addition to the effect as described in ① above, since the gastric juices are the water soluble liquid, the contents of the soft capsule in a form of oil may readily be dispersed in the gastric juices. Further, the direct infiltration of mastic into the, helicobacter pyloric bacteria may be facilitated, thus higher effect of the removal and inhibition of the helicobacter pyloric bacteria may be prospected. When ethanol or aqueous solution of ethanol is used as the amphipathic substance, the affinity of mastic with the gastric juices will increase, thus the removal and inhibition effects will increase as well.

③ In regard to the contents of the soft capsule which has been produced by dissolving mastic in the oils and fats, the case when the chitin or chitosan is further added, will now be discussed. In this case, due to acidic environment inside the stomach, chitin or chitosan will become positively charged, and since the inner wall of the stomach has generally been negatively charged, the chitin or chitosan will strongly adhere to the inner wall of the stomach. At that time, since the mastic will also adhere to the inner wall of the stomach together with the chitin or chitosan, the effective time of mastic to the helicobacter pyloric bacteria will become longer, and consequently, still higher effects of the removal and inhibition of the helicobacter pyloric bacteria may be expected.

④ The collection of mastic is carried out in a following method: That is, sap of mastic tree (Pistacia Lentiscus Var China). will first drop to the ground, and become solidified. Then, solid pieces of sap of mastic on the ground can be collected. Therefore, the thus collected mastic would be contaminated with impurities such as chips of wood, soil, insects, etc. In addition, since most of these impurities would be included inside the mastic resin, there has been no practical and effective method to purify the mastic. However, according to the present invention, since mastic has been dissolved in the oils and fats to be in a form of liquid during producing of the soft capsule, the impurities may easily be removed by filtration or sifting of the mastic oil, thus the purification of mastic can be accomplished without difficulty.

The purification of mastic can be carried out by any method other than to use the mastic oil. For example, mastic is first dissolved in ethanol, and then is filtrated or sifted to remove the impurities. The thus obtained fluid is then dried in order to volatilize the ethanol content, and eventually, the fine powder of mastic without impurity may be obtained. The powder of mastic may be dissolved again in oil in order to obtain the contents of the soft capsule according to the present invention. Further, the powder of mastic may also be used as the material hating no impurity, for producing chewing gum, hard capsule, tablet and other products containing mastic.

The following examples are illustrative of the methods of preparing the soft capsules including the comparative sample according to the prior art, and the clinical trials thereof, according to the present invention.

EXAMPLE 1

Preparation of Samples

The soft capsule samples 1 through 4 were prepared according to the present invention by the following methods. Further, the hard capsule sample 5 was prepared as a comparative sample according to the prior art.

(SAMPLE 1)

The mixture of 1000 g of mastic, and 1000 g of middle-chain fatty acid triglyceride ("ACTOR M-1" produced by Riken vitamin, a Japanese Company) was stirred in a hot bath at 60° C. for 30 minutes. Mastic was completely dissolved. This solution was then passed through a sift having the mesh screen at 50 μm in order to remove the impurities, and was cooled down to be at 25° C. Eventually the oil in which mastic was dissolved was obtained.

The thus obtained oil was then loaded in a soft capsule filling machine, and about 7000 pieces of soft capsule (type Oval No. 5), containing 225 mg of the said oil per capsule (that is, containing 112.5 mg of mastic per capsule), were produced by conventional producing method of ordinary soft capsule. The soft capsule obtained thereby was transparent and light yellow color, and the appearance thereof was so clear as to find no impurity therein.

(SAMPLE 2)

The mixture of 1000 g of mastic, 900 g of middle-chain fatty acid triglyceride ("ACTORM-1" produced by Riken Vitamin, a Japanese Company), and 100 g of glycerin fatty acid ester ("Decaglyn 3-0" produced by Nikko Chemicals, a Japanese Company) was stirred in a hot bath at 60° C. for 30 minutes. Mastic was completely dissolved. This solution was then passed through a sift having the mesh screen at 50 μm in order to remove the impurities, and was cooled down to be at 25° C. Eventually the oil in which mastic was dissolved, containing the surfactant, was obtained.

Thereafter, there were about 7000 pieces of soft capsule (type Oval No. 5), containing 225 mg of the said oil per capsule (that is, containing 112.5 mg of mastic per capsule), produced by almost the same method as that of Sample 1. The thus obtained soft capsule (Sample 2) was transparent and light yellow color, and the appearance thereof was so clear as to find no impurity therein.

(SAMPLE 3)

The mixture of 1000 g of mastic and 900 g of middle-chain fatty acid triglyceride ("ACTORM-1" produced by Riken Vitamin, a Japanese Company) was stirred in a hot bath at 60° C. for 30minutes. Mastic was completely dissolved. This solution was then passed through a sift having the mesh screen at 50 μm in order to remove the impurities, and was cooled down to be at 25° C. Then 100 g of chitosan ("Chitosan LL-80" produced by Kimitsu Kagaku, a Japanese Company) was added thereto. Eventually the oil in which mastic was dissolved, containing chitosan, was obtained. Thereafter, there were about 7000 pieces of soft capsule (type Oval No. 5), containing, 225 mg of the said oil per capsule (that is, containing 112.5 mg of mastic per capsule), produced by almost the same method as that of Sample 1. The thus obtained soft capsule (Sample 3) was translucent and light yellow color, and the appearance thereof was so clear as to find no impurity therein.

(SAMPLE 4)

The mixture of 1000 g of mastic, 700 g of middle-chain fatty acid triglyceride ("ACTOR M-1" produced by Riken Vitamin, a Japanese Company), and 300 g of aqueous solution of ethanol (concentration: 70%) was stirred in a hot bath at 60° C. for 30 minutes. Mastic was completely dissolved. This solution was then passed through a sift having the mesh screen at 50 μm in order to remove the impurities, and was cooled down to be at 25° C. Eventually the oil in which mastic was dissolved, containing the aqueous solution of ethanol, was obtained. Thereafter, there were about 7000 pieces of soft capsule (type. Oval No. 5), containing 225 mg of the said oil per capsule (that is, containing 112.5 mg of mastic per capsule), produced by almost the same method as that of Sample 1. The thus obtained soft capsule (Sample 4) was transparent and light yellow color, and the appearance thereof was so clear as to find no impurity therein.

(SAMPLE 5)

2000 g of mastic was coarsely crushed by a crusher ("wonder Blender WB-1" produced by Endo Kagaku, a Japanese Company) in order to obtain the grain at the size about granulated sugar. The thus obtained mastic grain was then loaded in a hard capsule filling machine, and was eventually filled in about 10000 pieces of vacant hard capsule (size No. 3, "Natural Hs No. 3" produced by Warner-Lambert). Each hard capsule contained 112.5 mg of mastic. There were several black impurities found in the hard capsule obtained thereby, and the appearance thereof was not clear.

(SAMPLE 6)

10 g of purified water was added to 10 g of the mastic grain which had been obtained according to SAMPLE 5 above, and this mixture was stirred in a hot bath at 37° C. for one hour. Then a filtrate serving as a sample 6 was eventually obtained by filtration of this mixture through a sterilizing filter at a caliber of 0.45 μm.

(SAMPLE 7)

10 g of artificial gastric juices (decay test agent fluid No. 1, according to the Japanese Pharmacopeia) was added to 10 g of the mastic grain which had been obtained according to SAMPLE 5 above, and this mixture was stirred in a hot bath at 37° C. for one hour. Then a filtrate serving as a sample 7 was eventually obtained by filtration of this mixture through a sterilizing filter at a caliber of 0.45 μm.

(Experiments)

The minimum Inhibitory Concentration (MIC) of each sample against the helicobacter pyloric bacteria was investigated according to the following experimental method:

① Each sample was dissolved in medium (BHI broth+Fetal Borine serum at 5%), and the sequential dilution was applied thereto.

② After the sequential dilution, the medium was injected in each hole of a 96-hole plate, for 0.1 ml per hole.

③ The medium of the helicobacter pyloric bacteria strain UL-6, which had been separated from a sufferer from gastric ulcer, was diluted to be at $10^7$ CFU/ml, and was eventually injected in each hole of the said 96-hole plate, for 5 μl per hole.

④ The contents of the 96-hole plate were cultured in a carbon dioxide gas incubator (the gas concentration at 5%), for three days at 37° C.

⑤ Thereafter, the multiplication of bacteria was observed by microscope, and the minimum Inhibitory Concentration (MIC) of each sample was investigated.

The result of MIC was as follows:
Sample 1 (soft capsule, mastic oil): 33 μg/ml
Sample 2 (soft capsule, mastic oil+surfactant): 25 μg/ml.
Sample 3 (soft capsule, mastic oil+chitosan): 20 μg/ml
Sample 4 (soft capsule, mastic oil+ethanol solution): 17 μg/ml
Sample 5 (hard capsule, grain of mastic): 119 μg/ml
Sample 6 (extract from mastic grain in water): 1250 μg/ml
Sample 7 (extract from mastic grain in artificial gastric juices): 1250 μg/ml
Sample 8 (artificial gastric juices): 2500 μg/ml As above illustrated, although the hard capsule according to the prior art even had the multiplication inhibitory effect in regard to the helicobacter pyloric bacteria, it was noted that the effect was much stronger in. every case of the soft capsule according to the present invention. In addition, both the extract from the mastic grain in the water, and the extract from the mastic grain in the artificial gastric juices had, although relatively small, in fact the multiplication inhibitory effect. However, as compared with the other samples according to the present invention, both the extract from mastic grain in water and the extract from mastic grain in artificial gastric juices had the seriously inferior multiplication inhibitory effect.

EXAMPLE 2

Clinical Trials

In regard to the soft capsule (Sample 1) of the present invention, the clinical trials were conducted for testees (20 persons) for the purpose of confirming the safety, effect and ingestion facility. Each testee ingested nine capsules (corresponding to 1 g of mastic) each day, for two-weeks.

The result was as follows:

① There was no one who claimed the bad physical condition. Consequently, according to the soft capsule of the present invention, there seemed to have no side effect which may occasionally be found in the conventional pharmaceutical.

② There were 12 testees among 20 testees who reported that the stomach condition became better or the indisposition of the stomach was disappeared in the course of the trials. This would imply the stomach improvement effect of the soft capsule according to the present invention.

③ All the testees answered that, as compared with the hard capsule in the prior art, the soft capsule according to the present invention had much ingestion facility. The difference of ingestion facility would be caused by the difference of weight between the soft and hard capsules. The weight of the hard capsule containing the grain of mastic is lighter than water, since the hard capsule also contains the air. On the other hand, the weight of the soft capsule according to the present invention is heavier than water, which may contribute to the ingestion facility. The ingestion facility according to the present invention would also be preferable for aged persons or children whose swallow ability are poor.

④ The present clinical trials brought about still another unexpected result. That is, three testees reported that, after starting the ingestion of the soft capsules, they felt that the smell of feces became reduced. This would imply that the soft capsule according to the present invention further had the possibility of reduction effect of the smell of feces.

EXAMPLE 3

Clinical Trials

For the purpose of confirming the reduction effect of the smell of feces by the soft capsule according to the present invention, there were another clinical trials conducted for. 10 testees who were all different from the testees of Example 2. The term and amount of ingestion of the soft capsule were the same as those of Example 2, and this time the reduction effect of the smell of feces was investigated.

The result was as per the following table.
(Table 1)

| Was the reduction effect of smell of feces confirmed? | Number of testees |
|---|---|
| Yes, there was the express effect | 3 |
| Felt that there was any effect | 5 |
| Hard to judge | 2 |
| No, there was no effect confirmed | 0 |
| Total | 10 |

As is clearly seen from the table as above illustrated, it was confirmed that the soft capsule according to the present invention had the remarkable reduction effect of smell of feces. According to the eight testees who reported the smell reduction effect, they began to feel that the smell of feces became reduced after about 1–3 days from the start of the ingestion.

EXAMPLE 4

Various Tests

For the purpose of confirming the effect of the soft. capsule according to the present invention in which the mastic oil is contained therein, there were still further tests done by the inventor. The results were as follows.
Test 4-1: Antibacterial Effect of Mastic Oil Against Helicobacter Pyloric Bacteria Derived from Human Sufferers
(Method of Test)

Each sample was dissolved in medium (BHI broth+Fetal Borine serum at 5%), and the sequential dilution was applied thereto. After the sequential dilution, the medium was injected in each hole of a 96-hole plate, for 0.1 ml per hole. The mediums of six types of the helicobacter pyloric bacteria strain separated from a sufferer, and a standard strain (NCTC) were diluted to be at $10^7$ CFU/ml, and were eventually injected in each hole of the said 96-hole plate, for 5 μl per hole. The contents of the 96-hole plate were cultured in a carbon dioxide gas incubator (the gas concentration at 5%), for three days at 37° C. Thereafter, the multiplication of bacteria was observed by microscope, and the minimum Inhibitory Concentration (MIC) of each sample was obtained.
(Result of Test)

TABLE 2-1

The minimum Inhibitory Concentration (MIC) of helicobacter pyloric bacteria derived from human sufferers, against mastic oil.

| Pyloric bacteria No. (Derived from) | Minimum Inhibitory Concentration |
|---|---|
| 22 (stomach cancer) | 0.050 mg/ml |
| 25 (stomach cancer) | less than 0.025 mg/ml |
| 26 (stomach cancer) | less than 0.025 mg/ml |
| 40 (stomach cancer) | 0.050 mg/ml |
| 1 (gastric ulcer) | 0.025 mg/ml |
| 27 (duodenal ulcer) | 0.050 mg/ml |
| 29 (duodenal ulcer) | 0.195 mg/ml |
| 5 (digestive organ disease) | 0.400 mg/ml |
| 6 (digestive organ disease) | 0.050 mg/ml |

TABLE 2-1-continued

The minimum Inhibitory Concentration (MIC) of helicobacter pyloric bacteria derived from human sufferers, against mastic oil.

| Pyloric bacteria No. (Derived from) | Minimum Inhibitory Concentration |
|---|---|
| 10 (digestive organ disease) | 0.400 mg/ml |
| 35 (digestive organ disease) | 0.050 mg/ml |
| 42 (malignant lymphoma) | 0.050 mg/ml |
| NCTC (standard strain) | 0.050 mg/ml |

(Measurement done at Department of Microorganism, School of Food and Nutritional Science, University of Shizuoka)

As above illustrated, the mastic oil displayed the superior antibacterial effect against various helicobacter pyloric bacteria derived from human being. Test 4-2: Antibacterial Effect of Mastic Oil Against General Bacteria
(Method of Test)

As to *Escherichia coli, Staphylococcus aureus*, and *Bacillus subtilis*, a typical strain of each bacterium was selected respectively. Then the minimum Inhibitory Concentration (MIC) of each strain against the mastic oil was obtained on the plate medium.
(Result of Test)

TABLE 2-2

The minimum Inhibitory Concentration (MIC) of general bacteria, against mastic oil.

| General bacteria strain | Minimum Inhibitory Concentration |
|---|---|
| *Escherichia coli* MC1061 | 16.0 mg/ml |
| *Staphylococcus aureus* 209P | 8.0 mg/ml |
| *Bacillus subtilis* | 2.0 mg/ml |

(Measurement done at Department of Oral Microbiology, Kanagawa Dental College)

As above illustrated, the mastic oil displayed the superior antibacterial effect against Escherichia coli, Staphylococcus aureus, and Bacillus subtilis.
Test 4-3: Antibacterial Effect of Mastic Oil Against Caries Pathogenic Bacteria and Periodontitis Pathogenic Bacteria
(Method of Test)

Six kinds of typical strains of caries pathogenic bacteria, and five kinds of typical strains of periodontitis pathogenic bacteria were selected respectively. Then the minimum Inhibitory Concentration (MIC) of each strain against the mastic oil was obtained on the plate medium.
(Result of Test)

TABLE 2-3

The minimum Inhibitory Concentration (MIC) of typical caries pathogenic bacteria and periodontitis pathogenic bacteria, against mastic oil.

| Strain type of caries pathogenic bacteria and periodontitis pathogenic bacteria | | Minimum Inhibitory Concentration (MIC) |
|---|---|---|
| Caries pathogenic bacteria | *Streptococcus mutans* 6751 | 4.0 mg/ml |
| | *Streptococcus sanguis* E206 | 4.0 mg/ml |
| | *Streptococcus mitis* | 4.0 mg/ml |

TABLE 2-3-continued

The minimum Inhibitory Concentration (MIC) of typical caries pathogenic bacteria and periodontitis pathogenic bacteria, against mastic oil.

| Strain type of caries pathogenic bacteria and periodontitis pathogenic bacteria | | Minimum Inhibitory Concentration (MIC) |
|---|---|---|
| | ATCC 9811 Actinomyces viscosus ATCC 15987 | 2.0 mg/ml |
| | Actinomyces naeslundii ATCC 12104 | 2.0 mg/ml |
| | Lactobacillus casei ATCC 393 | 2.0 mg/ml |
| Periodontitis pathogenic bacteria | Porphyromonas gingivalis 381 | less than 0.5 mg/ml |
| | Porphyromonas endodontalis ATCC 35406 | 16.0 mg/ml |
| | Prevotella intermedia ATCC 25261 | 16.0 mg/ml |
| | Fusobacterium nucleatum ATCC 25580 | less than 0.5 mg/ml |
| | Actinobacillus actinomycetem comitans ATCC 29523 | 2.0 mg/ml |

(Measurement done at Department of Oral Microbiology, Kanagawa Dental College)

As above illustrated, the mastic oil displayed the wider spectra and superior antibacterial effect against typical caries pathogenic bacteria and periodontitis pathogenic bacteria.

Test 4-4: The Comparative Test of Bacteria Inhibitory Effect Against Helicobacter Pyloric Bacteria, Between Mastic Oil, and Other Substances which have Actually Been Used as Pharmaceuticals or Foods Due to their Bacteria Inhibitory Effect Believed to Exist Against Helicobacterpyloric Bacteria (Method of Test)

Each sample was dissolved in medium (BHI broth+Fetal Borine serum at 5%), and the sequential dilution was applied. thereto. After the sequential dilution, the medium was injected in each hole of a 96-hole plate, for 0.1 ml per hole. The mediums of six types of the helicobacter pyloric bacteria strain separated from sufferer, and a standard strain (NCTC), were diluted to be at $10^7$ CFU/ml, and were eventually injected in each hole of the said 96-hole plate, for 5 µl per hole. The contents of the 96-hole plate were cultured in a carbon dioxide gas incubator (the gas concentration at 5%), for three days at 37° C. Thereafter, the multiplication of bacteria was observed by microscope, and the minimum Inhibitory Concentration (MIC) of each sample was obtained.

(Result of Test)

TABLE 2-4

Comparison of bacteria inhibitory effect against *helicobacter pyloric* bacteria, between mastic oil and other substances.

| | Minimum Inhibitory Concentration (MIC) for Inhibition of *helicobacter pyloric* bacteria (mg/ml) | | | | | |
|---|---|---|---|---|---|---|
| Pyloric bacteria No. (derived from) | Mastic oil | Bees wax | Licorice extract | Green tea extract | Lactobacillus agent (product of France) | Agent containing catechin (product of Japan) |
| 1 (gastric ulcer) | 0.025 mg/ml | 0.390 mg/ml | 0.390 mg/ml | | | |
| 22 (stomach cancer) | 0.050 mg/ml | 0.390 mg/ml | 0.195 mg/ml | | | |
| 26 (stomach cancer) | less than 0.025 mg/ml | 0.390 mg/ml | 0.195 mg/ml | | | |
| 42 (malignant lymphoma) | 0.050 mg/ml | 0.098 mg/ml | 0.195 mg/ml | | | |
| NCTC (standard strain) | 0.050 mg/ml | 0.390 mg/ml | 0.390 mg/ml | | | |
| 1 (gastric ulcer) | 0.037 mg/ml | | | | 5.000 mg/ml or more | 6.250 mg/ml 6.250 mg/ml |
| 50 (stomach cancer) | 0.037 mg/ml | | | | 5.000 mg/ml or more | 6.250 mg/ml 6.250 mg/ml |
| UL (duodenal ulcer) | 0.037 mg/ml | | | | 5.000 mg/ml or more | 6.250 mg/ml 6.250 mg/ml |
| NCTC (standard strain) | 0.073 mg/ml | | | | 5.000 mg/ml or more | 6.250 mg/ml 6.250 mg/ml |

(Measurement done at Department of Microorganism, School of Food and Nutritional Science, University of Shizuoka)

As above illustrated, the mastic oil displayed the superior antibacterial effect against helicobacter pyloric bacteria as compared with other substances and agents.

Test 4-5: Administrational Experiment of Mastic Oil to Testees Having the Subjective Symptom Such as a Pain or an Indisposition of the Stomach (Method of Test)

The administrational test of the soft capsule containing the mastic oil was done for seven male and female voluntary testees (generation: from 20's to 40's) who ordinarily had the subjective symptom such as a pain or indisposition of the stomach, or a poor appetite, which seemed to be caused by gastritis. The soft capsules containing mastic which had been dissolved in vegetable oil were administered to those testees for four weeks, and pursuit research was done in regard to the reduction of subjective symptom of each testee. The amount of ingestion of mastic was between 333 mg and 1000 mg per day, depending on the determination of the respective testees.

(Result of Test)

TABLE 2-5

The effect of mastic to voluntary testees having subjective symptom in the stomach.

| Subject of testees | Number of testees | Required period | Disappearance or remarkable improvement of subjective symptom — Number of testees whose symptoms disappeared or improved |
|---|---|---|---|
| Volunteers ordinarily having pain of indisposition of the stomach | 7 | 2–3 weeks of administration | 5 (71%) |

As above illustrated, in the second or third week after starting of the administration of mastic, five testees among seven (which may be said as a considerable high rate) reported the disappearance or improvement of subjective symptom.

Test 4-6: Anti-ulcerous Effect of Mastic Oil by Using Experimental Ulcerous Rats Under Immersion Restraint Stress (Method of Test)

TABLE 2-6-1

Experimental samples data

| Sample name | Tested substance | Solvent | Tested substance concentration | Amount of administered tested substance | Amount of administered fluid | Notes |
|---|---|---|---|---|---|---|
| Sample A | Mastic | MCT | 100 mg/ml | 500 mg/kg | 5 ml/kg | Note 1 |
| Sample B | Mastic | MCT | 4 mg/ml | 20 mg/kg | 5 ml/kg | Note 2 |
| Sample C | Mastic | Water | 100 mg/ml | 500 mg/kg | 5 ml/kg | Note 3 |
| Sample D | Yogurt | — | 100% | 5000 mg/kg | 5 ml/kg | Note 4 |
| Comparison E | — | — | 0 mg/ml | 0 mg/ml | 5 ml/kg | |

Note 1: The solution in which mastic was dissolved in MCT.
Note 2: See Note 1. The administrational amount of mastic corresponds to the ordinary ingestive amount of a human being per day.
Note 3: The supernatant in which mastic was dissolved in water, serving as the comparative to Note 1.
Note 4: The yogurt which had been reported to have the antibacterial effect against the pyrloric bacteria and anti-ulcerous effect. The administrational amount thereof corresponds to the ordinary ingestive amount of a human being per day.

As for the above five types of samples and comparison, eight SD-series male rats (aged six weeks) were respectively used per type of sample. The oral administration of sample was applied to eight rats per type of sample, and 30 minutes after administration, each rat was separately restrained in a cage having no space to move, and was immersed to the thoracic part thereof in a water bath at $23\pm2°$ C. for seven hours. After immersion, the rat was sacrificed, and the stomach was extracted in order to count the number of incidence of ulcers. The length of each ulcer was also measured.

The sum of the length of ulcers of each rat was obtained as the ulceration coefficient (mm). Further, the ulceration inhibitive rate (%) was obtained by comparing the sum of the ulceration coefficient of the comparative group E with the sum of the ulceration coefficient of each sample group.

(Result of Test)

TABLE 2-6-2

Result of test

| Sample name | Amount of administered tested substance | Ulceration coefficient (mm) | Ulceration inhibitive rate (%) |
|---|---|---|---|
| Sample A | 500 mg/kg of mastic | 14.0 ± 2.9 | 51.4 |
| Sample B | 20 mg/kg of mastic | 18.4 ± 3.9 | 36.1 |
| Sample C | 500 mg/kg of mastic | 27.1 ± 4.4 | 5.9 |
| Sample D | 5000 mg/kg of yogurt | 24.4 ± 4.2 | 15.3 |
| Comparison E | — | 28.8 ± 2.6 | — |

As above illustrated, by comparing with the comparison, the obtained inhibitive rate of the mastic oil rather tended to depend on the concentration, that is, the significant ulceration inhibitive effect thereof was confirmed at the high concentration. As for the mastic water solution and the yogurt, there was no clear ulceration inhibitive effect as compared with the comparison.

The soft capsule containing the mastic oil according to the present invention has the following merits.

First, as compared with the pharmaceutical such as an antibiotic or antibacterial agent, since the present invention uses mastic, that is the food material, there is no side effect, and higher safety can be secured.

Second, as compared with the product in the prior art in which the solid mastic is contained, higher inhibitory effect against the helicobacter pyloric bacteria can be obtained.

Third, since the product is in a form of soft capsule, the strong and unacceptable taste of mastic is concealed, thus the user may ingest the soft capsule easily. Further, although mastic itself is in a liquid form (oil), since the soft capsule can be treated as the solid product, the soft capsule can be handled conveniently.

Fourth, mastic is first dissolved in the oils and fats, ethanol or aqueous solution of ethanol, and the product is eventually produced by being filtrated or sifted. Therefore the mastic with high purity, having almost no impurities, may be ingested.

Fifth, the product according to the present invention may prevent the smell of feces which is the worst and strongest smell produced out of the human body.

The present invention is of course not limited to the embodiment and example as above discussed, as long as not departing from the spirit and scope of the invention. For example, there may be variation of amount of mastic contained. in each soft capsule, variation of mastic solvent contained in the soft capsule, or variation of material of the soft capsule.

What is claimed is:

1. A soft capsule filled with a Mastic oil, which comprises not more than 90 wt % Mastic, isolated from the Mastic tree, Pistacia lentiscus var China, dissolved in not less than 10 wt % of at least one liquid oil selected from the group consisting of fatty acids, short chain fatty acid glycerides, and middle-chain fatty acid glycerides.

2. The soft capsule as claimed in claim 1, further. comprising amphipathic substance added to said oils and fats.

3. The soft capsule as claimed in claim 2, wherein said amphipathic substance is a substance selected from the group consisting of a surfactant, an ethanol and an aqueous solution of ethanol.

4. The soft capsule as claimed in claim 1, further, comprising substance selected from the group of a chitin and a chitosan added to said oils and fats.

5. The soft capsule as claimed in claim 2, further comprising substance selected from the group of a chitin and a chitosan added to said oils and fats.

6. The soft capsule as claimed in claim 3, further comprising substance selected from the group of a chitin and a chitosan added to said oils and fats.

7. The soft capsule as claimed in claim 1, wherein said soft capsule serves reduction effect of smell of feces.

8. The soft capsule as claimed in claim 2, wherein said soft capsule serves reduction effect of smell of feces.

9. The soft capsule as claimed in claim 3, wherein said soft capsule serves reduction effect of smell of feces.

10. The soft capsule as claimed in claim 4, wherein said soft capsule serves reduction effect of smell of feces.

11. The soft capsule as claimed in claim 5, wherein said soft capsule serves reduction effect of smell of feces.

12. The soft capsule as claimed in claim 6, wherein said soft capsule serves reduction effect of smell of feces.

* * * * *